United States Patent
Wang et al.

[11] Patent Number: 5,873,811
[45] Date of Patent: Feb. 23, 1999

[54] COMPOSITION CONTAINING A RADIOACTIVE COMPONENT FOR TREATMENT OF VESSEL WALL

[75] Inventors: Lixiao Wang; Roger N. Hastings, both of Maple Grove, Minn.

[73] Assignee: Sci-Med Life Systems, Maple Grove, Minn.

[21] Appl. No.: 782,542

[22] Filed: Jan. 10, 1997

[51] Int. Cl.$^6$ .............................. A61M 29/02; A61N 5/10
[52] U.S. Cl. .................................................................. 600/5
[58] Field of Search ............................................. 600/1–8

[56] References Cited

U.S. PATENT DOCUMENTS

| | | | |
|---|---|---|---|
| 1,645,599 | 10/1927 | Jones | 600/1 |
| 4,799,479 | 1/1989 | Spears . | |
| 4,889,707 | 12/1989 | Day et al. | 600/3 |
| 5,030,194 | 7/1991 | Van't Hooft | 600/3 |
| 5,059,166 | 10/1991 | Fischell et al. | 600/3 |
| 5,084,001 | 1/1992 | Van't Hooft et al. | 600/3 |
| 5,092,834 | 3/1992 | Bradshaw et al. | 600/7 |
| 5,147,282 | 9/1992 | Kan | 600/1 |
| 5,176,617 | 1/1993 | Fischell et al. | 600/3 |
| 5,199,939 | 4/1993 | Dake et al. | 600/3 |

(List continued on next page.)

FOREIGN PATENT DOCUMENTS

| | | |
|---|---|---|
| 0 433 011 B1 | 6/1991 | European Pat. Off. . |
| 0 497 495 A2 | 8/1992 | European Pat. Off. . |
| 0 593 136 A1 | 4/1994 | European Pat. Off. . |
| 0 633 041 A1 | 1/1995 | European Pat. Off. . |
| 0 688 580 A1 | 12/1995 | European Pat. Off. . |
| 9102312.2 | 8/1992 | Germany . |
| 93/04735 | 3/1993 | WIPO . |
| 93/21970 | 11/1993 | WIPO . |
| 94/25106 | 11/1994 | WIPO . |
| 94/26205 | 11/1994 | WIPO . |
| 95/07732 | 3/1995 | WIPO . |

(List continued on next page.)

OTHER PUBLICATIONS

Raloff, "Nuclear Medicine Gets Friendlier—Experimental Therapies Seek to Poison Just the Disease", *Science News*, vol. 152, Jul. 19, 1997, pp. 40–41.

Fackelmann, "Harbinger of a Heart Attack—Does a Protein in the Blood Foretell Heart Trouble", *Science News*, vol. 151, Jun. 14, 1997, pp. 374–375.

"Aids and Cancer Cured by Hyper–oxygenation", *Now What*, Issue No. 1, 1987, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulsion The Question of Free Radicals", Internet Address http://www.livelinks.com/sumeria/oxy/rad2.html, Aug. 1, 1997.

(List continued on next page.)

*Primary Examiner*—John P. Lacyk
*Assistant Examiner*—Samuel Gilbert
*Attorney, Agent, or Firm*—Westman, Champlin & Kelly

[57] ABSTRACT

A method and composition for inhibiting restenosis. The composition includes an adhesive or polymeric material having a radioactive component dispersed therethrough. A biologically compatible adhesive including a radioactive material is applied to a vessel region where inhibition of restenosis is desired in a preferred method. In one composition, the radioactive material is admixed with the adhesive. In another composition, the radioactive material is chemically bonded to a polymeric adhesive. The adhesive is preferably cured in place. The radioactive material has a preferred half life of less than six months. In one method, the application of adhesive is followed by stent placement, leaving radioactive adhesive extending beyond both stent ends. The application can include forcing adhesive from a double walled balloon having a porous outer wall.

18 Claims, 2 Drawing Sheets

U.S. PATENT DOCUMENTS

| | | | |
|---|---|---|---|
| 5,213,561 | 5/1993 | Weinstein et al. | 600/7 |
| 5,213,580 | 5/1993 | Slepian et al. | 623/1 |
| 5,302,168 | 4/1994 | Hess | 600/3 |
| 5,308,356 | 5/1994 | Blackshear, Jr. et al. | 606/194 |
| 5,328,471 | 7/1994 | Slepian | 604/101 |
| 5,354,257 | 10/1994 | Roubin et al. | 600/7 |
| 5,411,466 | 5/1995 | Hess | 600/3 |
| 5,417,653 | 5/1995 | Sahota et al. | 604/20 |
| 5,421,826 | 6/1995 | Crocker et al. | 604/53 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,558,642 | 9/1996 | Schweich, Jr. et al. | 604/96 |
| 5,575,815 | 11/1996 | Slepian et al. | 623/1 |
| 5,605,530 | 2/1997 | Fischell et al. | 600/3 |
| 5,616,114 | 4/1997 | Thornton et al. | 600/3 |
| 5,618,266 | 4/1997 | Liprie | 604/21 |
| 5,634,946 | 6/1997 | Slepian | 623/11 |
| 5,643,171 | 7/1997 | Bradshaw et al. | 600/1 |
| 5,653,683 | 8/1997 | D'Andrea | 604/21 |
| 5,662,580 | 9/1997 | Bradshaw et al. | 600/3 |
| 5,662,609 | 9/1997 | Slepian | 604/101 |
| 5,674,177 | 10/1997 | Hehrlein et al. | 600/3 |
| 5,674,287 | 10/1997 | Slepian et al. | 623/11 |
| 5,683,345 | 11/1997 | Waksman et al. | 600/3 |

FOREIGN PATENT DOCUMENTS

| | | |
|---|---|---|
| 95/19807 | 7/1995 | WIPO . |
| 95/26681 | 10/1995 | WIPO . |
| 96/06654 | 3/1996 | WIPO . |
| 96/10436 | 4/1996 | WIPO . |
| 96/13303 | 5/1996 | WIPO . |
| 96/14898 | 5/1996 | WIPO . |
| 96/17654 | 6/1996 | WIPO . |
| 96/22121 | 7/1996 | WIPO . |
| WO 96/29943 | 10/1996 | WIPO . |
| WO 97/18012 | 5/1997 | WIPO . |
| WO 97/40889 | 11/1997 | WIPO . |

OTHER PUBLICATIONS

Barry, "Reactive oxygen Species in Living Systems—Source: Biochemistry, and Role in Human Disease", Internet Address http://www.livelinks.com/sumeria/oxy/reactive-.html, Jul. 21, 1997 from *American Journal of Medicine*, vol. 91, No. 3C, Sep. 30, 1991, p. 14S(9).

Block, "Peroxygen Compounds, Chapter 9", *Disinfection, Sterilization, and Preservation*, Fourth Edition, Lea & Febiger, Philadelphia, Copyright 1991.

Moore, "Free Radial Generation by Thyroid Peroxidase and Its Effects on Cells in Vitro", PhD. Dissertation, Group in Endocrinology—University of California, Berkeley, California, Dec. 1990.

Tjho–Heslinga et al., "Results of ruthenium irradiation of uveal melanoma", *Radiotherapy Oncology*, Fol. 29, pp. 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology*, vol. 232, pp. 482–487, 1994.

Nakayama et al., "Comparison of the Cytotyoxicity of Different Hydroperoxides to V79 Cells", *Free Rad. Res. Comms.*, vol. 14, No. 3, pp. 173–178.

Varma et al., "Hydrogen Peroxide in Human Blood", *Free Rad. Res. Comms*, vol. 14, No. 2, pp. 125–131.

Sutherland, "Managing Cancer Through Synergy", *Aministrative Radiology Journal*, Nov. 1996, pp. 21–27.

*Radiotherapty of Intraocular and Orbital Tumors*, Springer–Verlak publishers, Berlin Heidelberg and New York, copyright 1993, pp. 23–30 and 363–367.

Turiumi et al., "Histotoxicity of Cyanoacrylate Tissue Adhesives", *Arch Otolaryngol Head Neck Surg*, vol. 116, May 1990, pp. 546–550.

Otani et al., "A new biological glue from gelatin and poly(L–glutamic acid)", *Journal of Biomedical Materials Research*, vol. 31, pp. 157–166 (1996).

Guilmet et al., "Use of biological glue in acute aortic dissection", *Journal of Thoracic and Cardiovascular Surgery*, vol. 77, No. 4, Apr. 1979, pp. 516–521.

Matras, "Fibrin Seal: The State of the Art", *Max. Surg.*, pp. 605–611 (1985).

Kalmar et al., "Bioadhesives in Cardiac and Vascular Surgery", *Thorac. Cardiovasc. Surgeon*, vol. 30, 1982, pp. 230–233.

Ronis et al., "Review of Cyanoacrylate Tissue Glues with Emphasis on Their Otorhinolaryngological Applications", *Laryngoscope*, vol. 94, Feb. 1984, pp. 210–213.

*Fig.3*
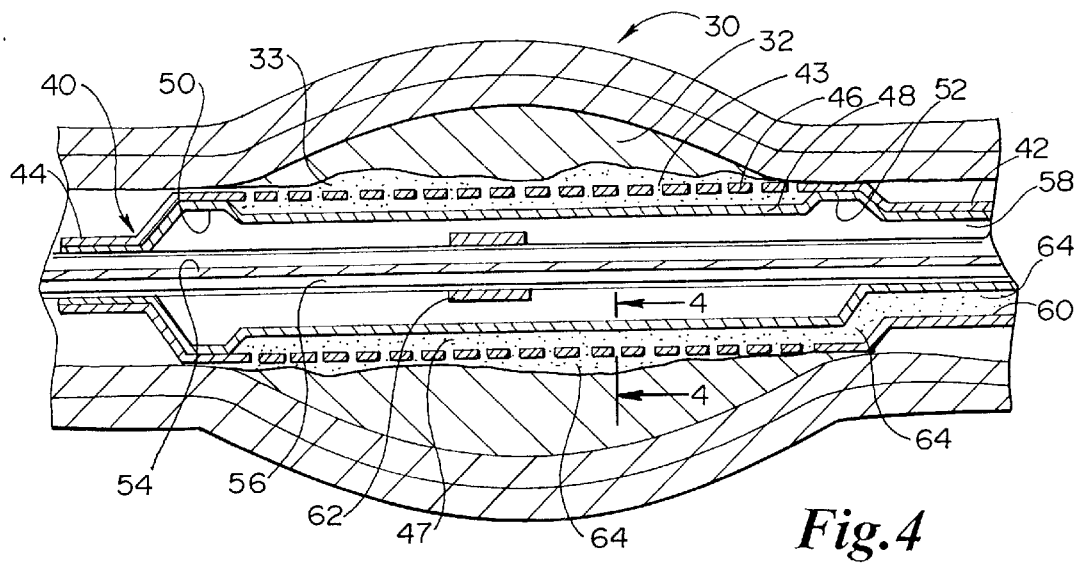
*Fig.4*
*Fig.5*
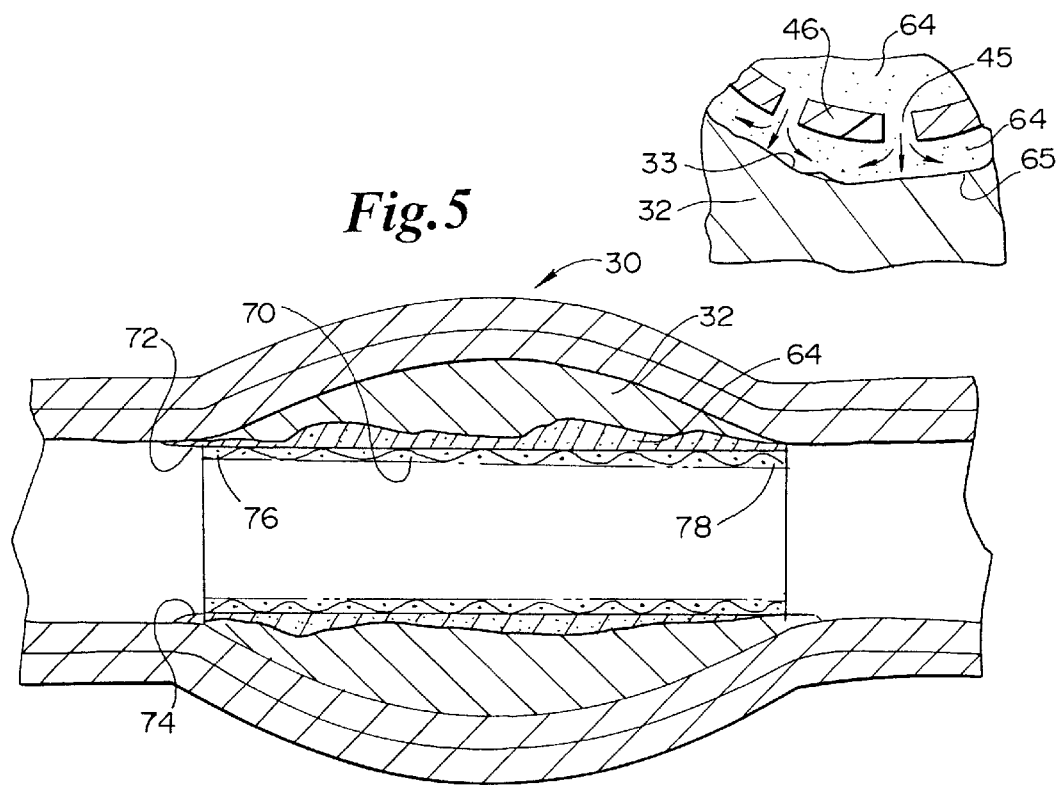

COMPOSITION CONTAINING A RADIOACTIVE COMPONENT FOR TREATMENT OF VESSEL WALL

FIELD OF THE INVENTION

The invention relates generally to a composition for application to a blood vessel wall which inhibits or prevents restenosis in coronary arteries after angioplasty, and methods for applying such composition. More specifically, the invention includes applying an adhesive or polymeric composition having a radioactive component therein to a vessel wall to inhibit restenosis.

BACKGROUND OF THE INVENTION

Coronary arteries provide blood and nutrients to the heart muscle. The arteries are subject to atherosclerosis or hardening of the arteries. Vascular regions have plaques formed within, resulting in stenosed regions having reduced cross-sectional area. The reduced area causes a reduction in transport of blood, oxygen, and nutrients which can result in angina, myocardial infarction and death.

A commonly used method for treating atherosclerosis is Percutaneous Transluminal Coronary Angioplasty (PTCA). PTCA includes insertion of a balloon catheter through an incision in the femoral artery near the groin, advancement of the balloon over the aortic arch, further advancement within the selected coronary artery, continuing until the balloon portion is placed across the stenosed region. The balloon is inflated, widening the narrowed vessel region.

After catheter withdrawal, significant vessel reclosure may develop. The reclosure may occur within hours or days of dilation, an "abrupt reclosure." When reclosure does occur, however, it more commonly occurs progressively, within six months of the angioplasty. The gradual reclosure is referred to as "restenosis", and largely negates the dilatation treatment. More highly stenosed vessel regions have a greater chance of becoming restenosed.

One approach to dealing with restenosis utilizes stents which are short tubular sections having a lumen therethrough, placed across the recently dilated vessel region. Stents can be either self-expanding or balloon-expandable. Stents are normally left in place indefinitely.

Stents, as any permanently implanted device, may possibly cause long term problems. As the stent is forever pushing radially outward against the vessel wall, the wall may be adversely affected over long time periods. Stent ends, which push radially outward, are adjacent to soft tissue which can be irritated by the stent end. Some believe the stent could promote restenosis in the region immediately beyond the stent ends. For this reason, the vessel may develop a new stenosed region adjacent either stent end. Stents commonly have wire mesh or spring structures, with openings in the stent walls. "Intimal hyperplasia", rapid tissue growth through stent openings has also been reported. While the exact mechanism of restenosis is not understood, it is believed that the vessel narrowing is due more to cellular growth mechanisms than to an elastic rebound mechanism.

Use of radiation to kill and inhibit growth of cancerous cells is well known. The use of radiation to inhibit restenosis has been proposed. U.S. Pat. No. 5,059,166 (Fischell et al.) proposes using a radioactive stent. Radioactive stents are indefinitely placed devices, with the possible irritating effects of stents. Furthermore, as stents are commonly formed of open structures such as springs or meshes, portions of vessel walls are exposed to radiation while other vessel areas more remote to stent wires, are exposed to much less radiation, if any. Further, the vessel cross section in a stenosed area may not conform to the stent shape and thus, the dose of radiation may vary due to proximity of the radioactive source to the vessel wall at any point.

Use of a catheter having a radioactive source on the distal end has been proposed in U.S. Pat. No. 5,199,939 (Dake et al.). The catheter must be held in place during the entire therapy, which is considerably shorter than the months long period over which restenosis is believed to occur. Any radiation delivered must be delivered within the short period the catheter tip is in place. The radiation dosage may be greater than that required if the exposure were more closely matched to the restenosis period. Centering the radioactive source within the vessel may be difficult, providing a greater dosage at the closer vessel wall than the further. The radiation source must be capable of reaching from catheter center, through any fluid, to vessel interior walls and beyond. This may require a more energetic, further penetrating source compared to that required if the radiation could be held directly and evenly over the vessel walls.

Use of adhesives in place of sutures in surgery is known. See, for example, "Histotoxicity of Cyanoacrylate Tissue Adhesives", 116 Arch Otolaryngol Head Neck Surg 546 (May 1990). See also "A New Biological Glue from Gelatin and Poly(L-glutamic acid)", 31 J. Biomedical Materials Res 157 (1996).

What is desirable and has not heretofore been provided is a method for inhibiting restenosis using radiation applied evenly, over long periods, without requiring stent placement. What would also be desirable is a method allowing for stent placement while inhibiting restenosis through stent walls and beyond the ends of the stent.

SUMMARY OF THE INVENTION

The present invention includes a method, composition and apparatus for inhibiting restenosis of a blood vessel following angioplasty and/or stent placement. More specifically, the method includes binding an adhesive or polymeric composition having a radioactive component therein to vessel walls of a recently dilatated region. It is believed the radioactivity inhibits restenosis by inhibiting cell growth.

The radioactive portion of the adhesive preferably has a half-life less than the six month period over which restenosis is believed to generally occur. It is also preferred that the half-life be longer than the period over which the stenosed region could be treated with radiation in an operating room. A preferred embodiment utilizes Beta emitters such as Phosphorus 32, which has a half-life of 14.3 days. It is believed that optimal results are achieved from more closely matching the radiation treatment period to the restenosis period.

The method also includes binding an adhesive having a growth factor therein to vessel walls. It is believed the growth factor inhibits restenosis by helping endothelialization. Suitable growth factors include fibroblast growth factor, epidermal growth factor, and transforming growth factor-B.

The adhesive has the radioactive material admixed in a preferred embodiment. In another embodiment, the radioactive material is incorporated into the backbone of the polymer or chemically bonded to a polymeric material or adhesive composition.

A variety of polymers may be utilized to practice the invention. A preferred adhesive is a hydrogel composed of gelatin and poly(L-glutamic acid)(PLGA). Another embodiment utilizes butyl-2-cyanoacrylate. Preferred adhesives are reactive adhesives which cure in place on the vessel wall. Curing mechanisms include polymerization and co-polymerization initiated chemically, thermally, by moisture, and by UV light. Optimally, the adhesives utilized are adsorbed by the body after the treatment period, leaving no permanent structure in place.

One method for applying the adhesive includes initiating the curing reaction outside the body and injecting the adhesive mixture through an adhesive delivery catheter to the stenosed region, after angioplasty. A preferred delivery device is a double walled balloon catheter having a porous outer envelope in addition to an inflatable inner envelope.

In use, the double walled balloon catheter is advanced to the treatment site over a guidewire. Once in place, the balloon is inflated, bringing the outer, porous envelope near and/or in contact with the inner surface of the stenosis and vessel. In one embodiment, proximal and distal balloon ends protrude to provide a tighter fit between outer envelope and vessel walls at either end than at balloon mid section.

With the inflated balloon in place, radioactive adhesive is forced from the porous outer envelope to the vessel inner wall. After allowing the adhesive sufficient time to cure, the balloon is deflated and the adhesive application device withdrawn. The radioactive material thus adheres closely enough for Beta radiation to effectively reach the cells likely to cause restenosis. The radioactivity is also spread more evenly than with wire stents or concentrated point radiation sources because the radiation source conforms to the shape of the vessel wall and is thus a constant distance from the vessel wall throughout any cross section of the vessel.

The radiation is thus applied in a low dose over a long period, directly to the region to be treated. The preferred adhesives are absorbed by the body rather than remain indefinitely.

In another embodiment, radioactive material is applied as described above, followed by or following stent placement. The radioactive adhesive preferably extends beyond the stents ends, inhibiting restenosis at the points where restenosis caused by stent irritation might otherwise occur.

BRIEF DESCRIPTION OF THE DRAWING

FIG. 3 is a similar view of the stenosed vessel of FIG. 2, having an adhesive applying catheter inserted within;

FIG. 4 is an enlarged sectional view of FIG. 3 taken along 4—4, illustrating adhesive flow from application device through outer envelope to stenosis wall; and FIG. 5 is a view similar to that of FIG. 3, of the stenosed region of FIG. 3 having adhesive and stent therein.

DETAILED DESCRIPTION OF THE PREFERRED EMBODIMENTS

Figure 1:
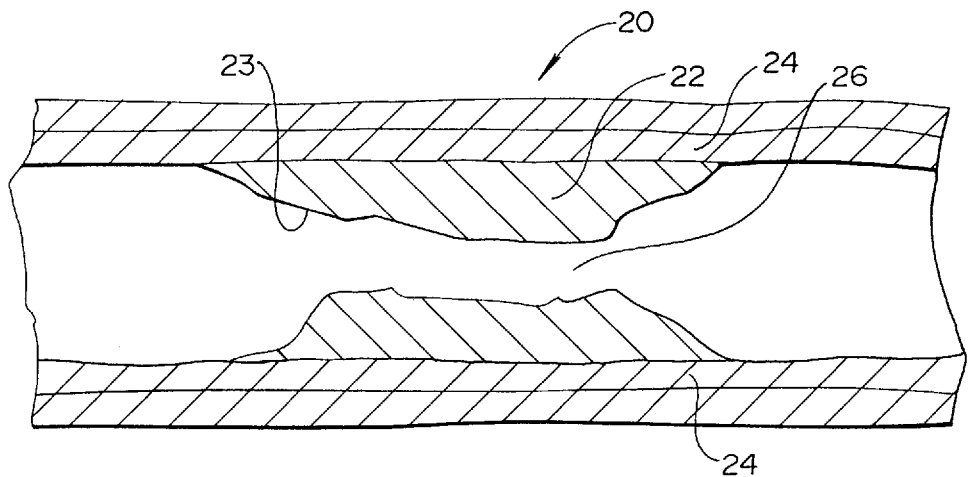
FIG. 1 is a fragmentary side elevational view of a stenosed vessel sectioned vertically on the vessel longitudinal axis.
Figure 2:
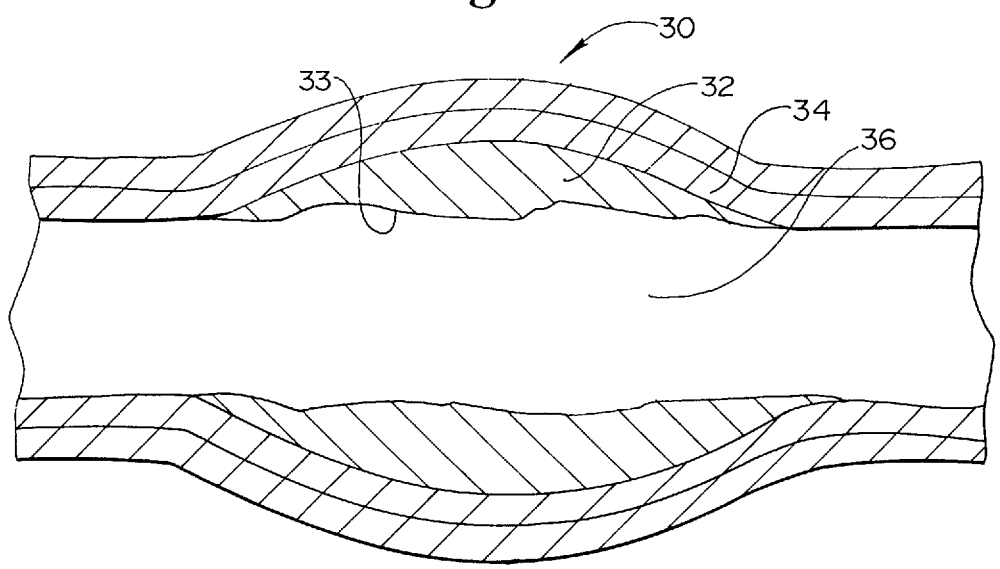
FIG. 2 is a similar view of the stenosed vessel of FIG. 1, after angioplasty.

FIG. 1 illustrates a stenosed vessel region 20 prior to angioplasty, including an inner vessel wall 24 having a stenosis 22 with an inner wall 23. Stenosis 22 creates a narrowed vessel channel 26. FIG. 2 illustrates a stenosed vessel region 30 after angioplasty, including an expanded inner vessel wall 34 having a compressed and widened stenosis 32 with a widened vessel channel 36. The present invention includes a method and apparatus for preventing the widened channel of FIG. 2 from restenosing to the narrowed channel of FIG. 1.

FIG. 3 illustrates stenosed region 30 after angioplasty, having an adhesive application device, here double walled balloon catheter 40, inserted in the vessel lumen in the stenosed region. Catheter 40 has a balloon 43 extending from balloon proximal end 42 to balloon distal end 44. Balloon 43 includes an inner envelope 48 and an outer, porous envelope 46. An interior space 47 lies between inner envelope 48 and outer envelope 46. The embodiment illustrated includes a proximal protrusion 52 and a distal protrusion 50, both shown extending in close proximity to vessel inner wall 24.

Catheter 40 is shown containing a guidewire 54 within a guidewire lumen 56. Catheter 40 also includes an inflation lumen 58 and an adhesive application lumen 60. A preferred embodiment includes a radiopaque marker band 62. A radioactive adhesive 64 is illustrated within lumen 60, within interior space 47, outside outer envelope 46, and in contact with stenosis inner surface 33. FIG. 4 illustrates in greater detail radioactive adhesive or polymeric composition containing a radioactive component 64 flowing at 65 through holes 45 in outer envelope 46 to stenosis inner surface 33. The contours and spaces between the catheter balloon 43 and the vessel wall 33, along with the thickness of adhesive composition 64 are not drawn to scale in FIGS. 3 and 4, but rather illustrate the application of the present invention.

FIG. 5 illustrates vessel region 30 after angioplasty, radioactive adhesive or polymer composition having a radioactive component application, and positioning of a stent 70 having a proximal end 78 and a distal end 76. Stent 70 has been expanded within radioactive adhesive 64. As illustrated, adhesive, at 72 and 74, extends beyond the end of stent 70.

A preferred embodiment includes Phosphorus 32 (P-32) as a radiation source. P-32 is a Beta emitter having a half-life of 14.3 days. Beta radiation has the advantage of low penetration, therefore adhesive or polymer composition containing P-32 will emit radiation that will penetrate or contact the vessel wall without unnecessarily penetrating into tissue further away. The two week half-life provides radiation over a longer period than possible with inserted catheter sources while not lasting beyond the desired six month restenosis period. Another potential embodiment contains Yttrium 90 (Y-90), a Beta emitter having a half-life of 64 hours.

Yet another embodiment utilizes Iridium 192 (Ir-192) as a radiation source. Ir-192 is a Gamma emitter having a half-life of 74.4 days. This has a longer half-life than P-32, yet well within the six month period. As a gamma emitter, more safety precautions must be taken in its use. Iodine 125 (I-125) is utilized in yet another embodiment mixtures of the above radiation source may be utilized.

In another aspect of the invention, growth factors can be utilized to inhibit restenosis. In one embodiment, growth factors are utilized in an adhesive mixture as an alternative to radioactive material. Applicants believe fibroblast growth factor, epidermal growth factor and transforming growth factor-B are suitable growth factors. Applicants believe growth factors inhibit restenosis by promoting or helping endothelialization. The various methods described in the present application relating to radioactive adhesives apply to growth factor adhesives as well.

Beta emitters have the advantage of penetrating into nearby vessel walls without penetrating unnecessarily into the human body. The relatively short penetration distance is not a problem as the invention insures the adhesive polymer composition is immediately adjacent the vessel wall.

A polymer, polymeric composition or adhesive is used to adhere the radioactive source closely to the vessel wall. Preferred adhesives are reactive adhesives, generally polymeric adhesives that cure in place, in contact with or adjacent the vessel wall. It is believed that a number of polymer families can be used, including polymers, copolymers, and monomers having multi-functional groups in general. Various methods of polymerization initiation are well known. In one embodiment, monomer and chemical initiators are mixed outside the body and injected through a catheter lumen proximal port, flowing to the site to be treated.

In another method, monomers are injected through a catheter lumen proximal port, flowing to the site to be treated, and polymerization initiated inside the body. Initiation is accomplished in one embodiment utilizing chemical initiators pre-loaded near the catheter distal region. This is accomplished in one embodiment by providing cross-linking agents which initiate the reaction. In still another embodiment, polymerization is initiated chemically by forcing two separate streams from a catheter distal region, mixing occurring primarily near the vessel wall after compounds leave the delivery device.

In another embodiment, initiation is performed using an ultra-violet light source inserted into the stenosed region after coating the region with monomer. UV initiation is performed in another embodiment while the vessel walls are being coated. In yet another embodiment, initiation is commenced by forcing monomer past a UV source within the catheter, preferably in the distal region.

In yet another embodiment, polymerization is heat initiated. The heat in one variation is obtained from body heat. In another variation, heat is supplied by the catheter.

A preferred method of delivery includes inflating a balloon having an adhesive covering a substantial portion of the balloon. The curing adhesive is thus held in place against the vessel wall, promoting adhesion and lessening any loss of adhesive material to blood flow within the vessel. A preferred catheter for delivery is a perfusion balloon catheter. A catheter allowing perfusion therethrough allows holding adhesive against the vessel walls for longer curing times while allowing blood to flow through the coronary artery. Examples of catheters suitable for adhesive application are drug delivery catheters as disclosed in U.S. Pat. No. 5,558,642, entitled "Drug Delivery Catheter" or U.S. Pat. No. 5,554,119, entitled "Drug Delivery Catheter with Manifold", the disclosures of which are incorporated herein by reference. Another suitable catheter is disclosed in U.S. patent application Ser. No. 08/441,168, filed May 15, 1995, entitled "Perfusion Balloon Angioplasty Catheter" to the present assignee, the disclosure of which is incorporated herein by reference. This disclosed catheter can be constructed with a porous drug delivery member over the balloon, as illustrated in FIG. 3.

In yet another embodiment, a balloon envelope is coated with a viscous or otherwise difficult to inject adhesive mixture. The balloon envelope and a sheath are advanced coextensively until reaching the treatment site. The sheath is then withdrawn, polymerization initiated and balloon expanded, forcing the adhesive mixture against the vessel wall. Relative order of balloon expansion and initiation depend upon the adhesive chosen. In a variation on this embodiment, a stent placement balloon with stent mounted thereover is coated with an adhesive mixture extending fore and aft of the stent. The stent is expanded into place against the vessel wall, positioning the adhesive mixture against the vessel wall as well. Polymerization can be initiated before or after positioning the adhesive against the vessel wall. A variation on this method utilizes a thick layer of adhesive mixture over the stent, such that expanding the stent against the vessel wall forces excess adhesive beyond the stent ends, along the vessel walls.

In one method, vessel walls are coated with adhesive prior to stent placement. This can be accomplished with a catheter delivery device distinct from the stent placement device. In one method the stent is delivered first, followed by delivery of the radioactive adhesive over the stent, beyond the ends of the stent, and between the stent struts to exposed tissue.

While the adhesive serves to hold radioactive material close to the vessel walls, advantage can be taken of the adhesive structural properties. The polymerized material, if sufficiently strong, can serve as a stent, providing radially outward support against restenosis. See for example, U.S. Pat. No. 5,213,580 (Slepian et al.) proposing use of polycaprolactone to coat dilated regions to prevent restenosis, herein incorporated by reference.

The adhesive chosen must be sufficiently biocompatible so as to not cause long term vessel damage. The adhesive chosen must also not generate such excessive heat of polymerization so as to harm the vessel wall.

A preferred adhesive is a hydrogel composed of gelatin and poly(L-glutamic acid)(PLGA). The hydrogel is formed by chemically cross linking gelatin and poly(L-glutamic acid). Another preferred adhesive is fibrin glue. One suitable fibrin glue includes fibrinogen, thrombin, calcium chloride and factor VIII. Another family of adhesives is cyanoacrylates. Preferred cyanoacrlates include butyl-2-cyanoacrylate (Histoacryl), ethyl-2-cyanoacrylate, and octyl-2-cyanoacrylate. Gelatin-resorcinol formaldehyde-glutaraldehyde is another suitable adhesive.

Applicants believe many polymers having suitable adhesive properties can be utilized, including without limitation: polyurethanes having amino groups, di- and tri-functional diols; polyvinyl acetates; polyamides; polyvinyl alcohols; polystyrenes; polylactides; polyactones; block copolymers including polyesters, polyamides, and polyurethanes; and combinations and mixtures thereof.

In a preferred embodiment, the radioactive material is admixed with the adhesive. In another embodiment, the polymer structure itself, such as the polymer backbone, includes a radioactive material. Polymers including chemically bonded pendent phosphate groups having P-32 are within the scope of the invention. Phosphorus-32 containing amino acids are commercially available and incorporation within polymeric adhesives is explicitly contemplated. In yet another embodiment, non-covalent bonds bind radioactive material to the adhesive. For example, chelation can be used to bind radioactive materials. Salts of radioactive compounds, I-125 for example, can be mixed within the adhesive.

It is believed that providing radioactivity at a lower rate over a long time period results in restenosis inhibition results superior to those resulting from higher radioactivity rates over a shorter time period. This could be the result of constant inhibition of cell growth being superior to damaging cells in a short period at the outset. A preferred dosage is in the range of 0.1 to 10 microCurie total activity delivered to the treatment site.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed:

1. A method for inhibiting restenosis at a vessel wall region comprising the steps:

providing an adhesive including a radioactive material; and applying said adhesive to said vessel wall region.

2. A method as recited in claim 1 wherein said radioactive material is admixed with said adhesive.

3. A method as recited in claim 1 wherein said radioactive material is chemically bonded to said adhesive.

4. A method as recited in claim 1 wherein said radioactive material is selected from the group consisting of: Phosphorus 32, Yttrium 90, Iodine 125, Iridium 192, and mixtures thereof.

5. A method as recited in claim 1 wherein said adhesive includes polymeric material and said radioactive material is bonded to said polymeric material.

6. A method as recited in claim 1 wherein said applying step includes:

providing a catheter including adhesive application means;

advancing said catheter adhesive application means to said vessel wall region; and applying said adhesive utilizing said catheter adhesive application means.

7. A method as recited in claim 6 wherein said adhesive application means is a balloon catheter including a first lumen having a distal opening, an inner inflatable envelope and an outer envelope having a space therebetween, said outer envelope having a plurality of holes therein, said outer envelope having an inner wall in fluid communication with said first lumen, said applying step further including:

inflating said first envelope within said vessel wall region; and forcing said adhesive distally from said first lumen distal opening into said space, through said holes to said vessel wall region.

8. A method as recited in claim 7 wherein said catheter includes a proximal end and said first lumen includes a proximal end and a proximal opening, said forcing step further including injecting said adhesive into said first lumen proximal opening.

9. A method as recited in claim 7 further comprising placing a stent within said vessel wall region.

10. A composition for use in inhibiting restenosis in a body comprising an adhesive composition and a radioactive material dispersed therethrough, wherein the adhesive composition is adapted to be absorbed by the body after a period of time.

11. The composition of claim 10 wherein said radioactive material is admixed with said adhesive.

12. The composition of claim 10 wherein said radioactive material is part of the structure of said adhesive.

13. The composition of claim 10 wherein said radioactive material is selected from the group consisting of: Phosphorus 32, Yttrium 90, Iodine 125, Iridium 192, and mixtures thereof.

14. The composition of claim 10 wherein said adhesive composition includes a polymeric material and said radioactive material is bonded to said polymeric material.

15. A composition for use in inhibiting restenosis comprising an adhesive composition and a radioactive material dispersed therethrough, wherein said adhesive composition is a moisture cure adhesive selected from the group consisting of: fibrin glue and cyanoacrylates.

16. The composition of claim 15 wherein said fibrin glue includes fibrinogen, thrombin, calcium chloride and factor VIII.

17. The composition of claim 15 wherein said cyanoacrylate is selected from the group consisting of: butyl-2-cyanoacrylate, ethyl-2-cyanoacrylate, octyl-2-cyanoacrylate, and mixtures thereof.

18. A method for inhibiting cell growth in a tissue region of a human body comprising the steps:

providing an adhesive including a radioactive material;

applying said adhesive to said tissue region; and allowing said adhesive to cure while said adhesive is applied to said tissue region.

* * * * *